United States Patent [19]

Tanonaka et al.

[11] Patent Number: 4,814,521

[45] Date of Patent: Mar. 21, 1989

[54] PROCESS FOR PRODUCING 2,6-DIHYDROXYNAPHTHALENE AND 2,6-DIACETOXYNAPHTHALENE

[75] Inventors: Takayuki Tanonaka; Takashi Yamauchi; Hiroyuki Enari; Yutaka Konai, all of Iwaki, Japan

[73] Assignee: Kureha Kagaku Kogyo Kabushiki Kaisha, Tokyo, Japan

[21] Appl. No.: 89,661

[22] Filed: Aug. 26, 1987

Related U.S. Application Data

[63] Continuation-in-part of Ser. No. 870,841, Jun. 5, 1986, abandoned, and a continuation-in-part of Ser. No. 73,470, Jul. 15, 1987, abandoned.

[30] Foreign Application Priority Data

Jun. 7, 1985 [JP] Japan .................................. 60-123819
Sep. 20, 1985 [JP] Japan .................................. 60-208372
Jul. 15, 1986 [JP] Japan .................................. 61-166080

[51] Int. Cl.$^4$ ..................... C07C 37/01; C07C 41/00; C07C 43/20
[52] U.S. Cl. .................................. 568/741; 568/629; 568/631; 568/633; 568/771; 568/803
[58] Field of Search ............... 568/768, 737, 803, 741, 568/629, 771, 631, 633

[56] References Cited

U.S. PATENT DOCUMENTS

| | | | |
|---|---|---|---|
| 3,481,989 | 12/1969 | Vesely et al. ....................... | 568/741 |
| 3,600,446 | 8/1971 | Massie ................................ | 568/741 |
| 3,816,545 | 6/1974 | Block ................................. | 568/741 |
| 4,045,496 | 8/1977 | Seifert et al. ...................... | 568/629 |
| 4,174,460 | 11/1979 | Seifert et al. ...................... | 568/629 |
| 4,214,105 | 7/1980 | Seifert et al. ...................... | 568/771 |
| 4,324,925 | 4/1982 | Jupe et al. ......................... | 568/741 |
| 4,533,766 | 8/1985 | Drauz et al. ....................... | 568/741 |
| 4,590,305 | 5/1986 | Drauz et al. ....................... | 568/771 |

FOREIGN PATENT DOCUMENTS 2090827 7/1982 United Kingdom ............... 568/741

OTHER PUBLICATIONS

J. Org. Chem., vol. 15, pp. 775–781 (1950).
Houben–Weyl, Methoden der Organischen Chemie, Band 6/16, Seiten 133–134 (1976).

*Primary Examiner*—Warren B. Lone
*Attorney, Agent, or Firm*—John P. White

[57] ABSTRACT

Disclosed herein is a process for producing 2,6-dihydroxynaphthalene which comprises oxidizing 2,6-di(2-hydroxy-2-propyl)naphthalene in acetonitrile, 1,4-dioxane or a mixture thereof with hydrogen peroxide in the presence of an inorganic acid or a solid acid at a temperature in the range of room temperature to the boiling point of the solution of the 2,6-di(2-hydroxy-2-propyl)naphthalene in acetonitrile or 1,4-dioxane, the acetonitrile, 1,4-dioxane or a mixture thereof being used in an amount of 3 to 30 ml to one gram of the 2,6-di(2-hydroxy-2-propyl)naphthalene.

17 Claims, No Drawings

PROCESS FOR PRODUCING 2,6-DIHYDROXYNAPHTHALENE AND 2,6-DIACETOXYNAPHTHALENE

CROSS-REFERENCE TO RELATED APPLICATION

The present application is a continuation-in-part of application Ser. No. 870,841 filed June 5, 1986 and of application Ser. No. 073,470, filed July 15, 1987 now both abandoned.

BACKGROUND OF THE INVENTION

The present invention relates to a process for producing 2,6-dihydroxynaphthalene and highly pure 2,6-diacetoxynaphthalene which are utilized as the monomer of aromatic polyesters having an ability of forming liquid crystalline polymers.

More in detail, the present invention relates to a process for producing 2,6-dihydroxynaphthalene, which comprises oxidizing 2,6-di(2-hydroxy-2-propyl)naphthalene in acetonitrile, 1,4-dioxane or a mixture thereof with hydrogen peroxide in the presence of an inorganic acid or a solid acid at a temperature in the range of room temperature to the boiling point of the solution of 2,6-di(2-hydroxy-2-propyl)naphthalene in acetonitrile or 1,4-dioxane, the acetonitrile, 1,4-dioxane or a mixture thereof being used in an amount of 3 to 30 ml to one gram of the 2,6-di(2-hydroxy-2-propyl)naphthalene, and a process for producing a highly pure 2,6-diacetoxynaphthalene by acetylating the thus obtained 2,6-dihydroxynaphthalene.

In recent years, various engineering plastics have been developed, and as the plastics in this field, aromatic polyesters, particularly those having an ability of forming liquid crystalline polymers have attracted one's attention.

As the starting material for the aromatic polyesters having an ability of forming liquid crystalline polymers, terephthalic acid, hydroquinone, p-hydroxybenzoic acid, etc. may be mentioned, however, in order to improve the physical and/or chemical properties of the aromatic polyesters, not only the benzene compounds but also naphthalene compounds have come to be required as the starting material thereof.

Of the naphthalene compounds, 2,6-dihydroxynaphthalene and 2,6-diacetoxynaphthalene have attracted one's attention as the monomers utilized in the production of the aromatic polyesters from the viewpoints that the physical properties of the liquid crystalline polymers obtained therefrom are excellent and terephthalic acid used as the comonomer thereof is available at a low price.

Although 2,6-diacetoxynaphthalene is obtained by acetylation of 2,6-dihydroxynaphthalene, since 2,6-dihydroxynaphthalene is not produced industrially at present, there is a problem that 2,6-diacetoxynaphthalene is not available inexpensively.

In this connection, as the process for producing 2,6-dihydroxynaphthalene, a classic process has hitherto been known, wherein naphthalene or β-naphthol is sulfonated and the thus sulfonated product is subjected to alkali fusion. Such a process is described in Beilstein's "Handbuch der organischen Chemie". However, according to this process, for instance, as seen from Japanese Patent Publication No. 56-77254 (1981), by-production of the other isomers than 2,6-isomer is inevitable in the sulfonation step and accordingly, the 2,6-isomer cannot be obtained in a high yield. Further, in the alkali fusion step, for instance, as is described in A. P. Kuriakose et al. J. Indian Chem. Soc., 43, 437 (1966), since the yield of 2,6-dihydroxynaphthalene is as low as 50%, the total yield of 2,6-dihydroxynaphthalene in this process wherein naphthalene or β-naphthol is sulfonated and the thus sulfonated product is subjected to alkali fusion is extremely low.

In addition, it is necessary to provide the draining treatment in the step of alkali fusion and accordingly, there is a problem of increased cost. Namely, the process is industrially poor in practicality.

Besides, a process for producing hydroquinone from p-isopropylbenzene, while applying "the cumene process" has hitherto been known (Japanese Patent Publication No. 51-33100 (1976) and the following process for producing 2,6-dihydroxynaphthalene could be considered.

Namely, while applying the process to the production of 2,6-dihydroxynaphthalene, 2,6-diisopropylnaphthalene is oxidized and the thus obtained dihydroperoxide is subjected to acid decomposition to be converted into 2,6-dihydroxynaphthalene [refer to Japanese Patent Applications Laid-Open (KOKAI) Nos. 61-93 156 (1986), 61-100 558 (1986) and 61-191 638 (1986)].

However, in such a process, since the yield of the dihydroperoxide is poor as compared to that of the process for producing hydroquinone and it is difficult to isolate the thus formed dihydroperoxide, the above-mentioned process for producing 2,6-dihydroxynaphthalene cannot be said to be industrially suitable.

On the other hand, a process wherein a compound represented by the formula:

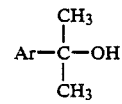

wherein Ar represents an aromatic ring, is oxidized in a solvent with hydrogen peroxide in the presence of a strong acid into a phenolic compound represented by the formula, Ar-OH, has been also known (for instance, refer to Japanese Patent Application Laying-Open (KOKAI) No. 52-5718 (1977), Japanese Patent Publication No. 35-7558 (1960), British Patent No. 910,735, TSUNODA and KATO J. Chem. Soc. Japan, 80 (7), 689 (1959) and M. S. Kharasch et al. J. Org. Chem., 15, 748 and 775 (1950)). However, the reaction disclosed in the references are processes for converting (2-hydroxy-2-propyl)benzene, p-di(2-hydroxy-2-propyl)benzene, 1-(2-hydroxy-2-propyl)-4-(2-hydroperoxy-2-propyl)-benzene, etc. into phenol or hydroquinone.

Further, U.S. Pat. No. 4,214,105 discloses a process for producing pyrocatechol and hydroquinone wherein phenol is reacted with substantially anhydrous hydrogen peroxide dissolved in a non-aqueous solvent, the reaction being carried out in the presence of a strong acid at a temperature of 20°-150° C. in a reaction mixture containing hydrogen peroxide, solvent, phenol and strong acid.

Also, U.S. Pat. No. 4,503,262 discloses a process for the conversion of 2,6-diisopropylnaphthalene to 2,6-diisopropylnaphthalene hydroperoxide with an oxygen-containing gas in $C_5$-$C_{14}$ aliphatic hydrocarbons in the presence of a catalytically active heavy metal compound, and discloses the following:

"The 2,6-diisopropylnaphthalene dihydroperoxide of this invention can be converted to the corresponding 2,6-dihydroxynaphthalene which is a known starting monomer for the production of polymers. The convention of the dihydroperoxide to the corresponding dihydroxy compound is well known in the art and involves reaction of the hydroperoxide in an acidic medium. Techniques of this type are disclosed in U.S. Pat. Nos. 3,927,124; 3,884,983; 3,928,469; 3,923,908; and 3,900,423, the disclosures of which are incorporated herein by reference."

However, there is no disclosure concerning the process for converting a compound having naphthalene ring such as di(2-hydroxy-2-propyl)naphthalene, etc. into dihydroxynaphthalenes in the references.

In this connection, it is substantially impossible to obtain 2,6-dihydroxynaphthalene profitably in industrial scale from 2,6-di(2-hydroxy-2-propyl)naphthalene (hereinafter referred to as 2,6-DHPN) by the process disclosed in the references due to the following reason.

Namely in oxidizing 2,6-DHPN in the solvent used in the process disclosed in the references (1) 2,6-DHPN does not dissolve in the solvent described in the references, (2) in spite of the disappearance of 2,6-DHPN from the reaction system, 2,6-dihydroxynaphthalene is scarcely formed, (3) the solvent itself reacts in the system or (4) the reaction rate is very low.

The above-mentioned facts are considered to be due to the remarkable difference of the physical and/or chemical properties between the naphthalene compound (2,6-DHPN) and the benzene compound ((2-hydroxy-2-propyl)benzene, etc.).

As a result of the present inventors' studies on the industrially profitable process for producing 2,6-dihydroxynaphthalene and 2,6-diacetoxynaphthalene, it has been found by the present inventors that (1) 2,6-dihydroxynaphthalene can be profitably produced by using 2,6-DHPN as the starting material, which is available from 2,6-diisopropylnaphthalene which is easily available in an industrial scale and subjecting 2,6-DHPN to oxidation under specified conditions, and (2) 2,6-diacetoxynaphthalene of a high purity can be produced in a high yield by further acetylating the thus obtained 2,6-dihydroxynaphthalene, and based on the findings, the present inventors have attained the present invention.

Namely, the object of the present invention is to provide a process for advantageously and industrially producing 2,6-dihydroxynaphthalene which is useful as the raw material for producing the so-called liquid crystal polymers which has a capacity of forming liquid crystals.

SUMMARY OF THE INVENTION

In a first aspect of the present invention, there is provided a process for producing 2,6-dihydroxynaphthalene which comprises oxidizing 2,6-DHPN in acetonitrile, 1,4-dioxane or a mixture thereof with hydrogen peroxide in the presence of an inorganic acid or a solid acid at a temperature in the range of room temperature to the boiling point of the solution of the 2,6-DHPN in acetonitrile or 1,4-dioxane, the acetonitrile, 1,4-dioxane or a mixture thereof being used in an amount of 3 to 30 ml to one gram of the 2,6-DHPN.

In a second aspect of the present invention, there is provided a process for producing 2,6-dihydroxynaphthalene, which comprises oxidizing 2,6-DHPN in acetonitrile, 1,4-dioxane or a mixture thereof with hydrogen peroxide in the presence of an inorganic acid of an amount not less than 0.001 time by weight and less than 0.1 time by weight to the amount of the 2,6-DHPN at a temperature in the range of 60° C. to the boiling point of the solution of the 2,6-DHPN in acetonitrile or 1,4-dioxane, the acetonitrile, 1,4-dioxane or a mixture thereof being used in an amount of 7 to 25 ml to one gram of the 2,6-DHPN.

In a third aspect of the present invention, there is provided a process for producing 2,6-diacetoxynaphthalene of high purity, which comprises oxidizing 2,6-DHPN in acetonitrile, 1,4-dioxane or a mixture thereof with hydrogen peroxide in the presence of an inorganic acid or a solid acid under the conditions of the first aspect or second aspect, and acetylating the thus obtained 2,6-dihydroxynaphthalene at a temperature in the range of 100° to 140° C. for 30 minutes to 2 hours thereby obtaining 2,6-diacetoxynaphthalene

DETAILED DESCRIPTION OF THE INVENTION

The present invention relates to (1) a process for producing 2,6-dihydroxynaphthalene by oxidizing 2,6-DHPN in acetonitrile, 1,4-dioxane or a mixture thereof with hydrogen peroxide in the presence of an inorganic acid or a solid acid and (2) a process for producing 2,6-diacetoxynaphthalene by acetylating 2,6-dihydroxynaphthalene obtained by the process shown in (1).

2,6-DHPN used as the starting material according to the present invention can be easily obtained by applying the known process for producing dimethylphenylcarbinol from cumene to 2,6-diisopropylnaphthalene.

It is important in the present invention to use acetonitrile, 1,4-dioxane or a mixture thereof as the solvent in oxidizing 2,6-DHPN into 2,6-dihydroxynaphthalene. As has been described, in the case of using another solvent in the above-mentioned reaction, it is difficult to obtain 2,6-dihydroxynaphthalene profitably in an industrial scale. For instance, ketones such as acetone, isobutyl methyl ketone, etc. used as the solvent in the Japanese Patent Publication No. 52-5718 (1977) are not inert to the reaction and accordingly, in the case of using such a solvent in the present reaction, although 2,6-dihydroxynaphthalene is formed, a large amount of by-products derived from ketone is formed.

In addition, in the case of using a lower alcohol such as methanol, ethanol, 2-propanol, etc. as the solvent, the reaction rate is very small and in addition, the selectivity in reaction is low and consequently, it is impossible to obtain 2,6-dihydroxynaphthalene in a high yield.

Furthermore, in the case of using a lower fatty acid such as acetic acid, propionic acid, etc. as the solvent, although 2,6-DHPN disappears from the reaction system, 2,6-dihydroxynaphthalene is scarcely formed because of the preferential side reactions. In addition, in the case of using a hydrocarbon as the solvent, since the solubilities of 2,6-DHPN and 2,6-dihydroxynaphthalene (which is the reaction product) in such a solvent are very small, it is impossible to obtain 2,6-dihydroxynaphthalene in a high yield.

The reaction temperature of the process for producing 2,6-dihydroxynaphthalene according to the present invention may be selected in the range of from room temperature to the boiling point of the solution of the 2,6-DHPN in acetonitrile or 1,4-dioxane.

Preferred temperature is as follows:

In the method (I), the oxidation is carried out at a temperature in the range of room temperature to 80° C., more preferable 30° to 60° C.

In the method (II), the oxidation is carried out at a temperature in the range of 60° C. to the boiling point of the solution of the 2,6-DHPN in acetonitrile or 1,4-dioxane, more preferable 65° to 80° C.

Although the reaction period depends on the amount of 2,6-DHPN, the solvent, the inorganic acid or the solid acid and hydrogen peroxide used in the reaction and the reaction temperature, the reaction ordinarily completes in the range of from 10 min to 3 hours.

According to the present invention, acetonitrile, 1,4-dioxane or a mixture thereof is used as the solvent in an amount of 3 to 30 ml, preferably 5 to 20 ml to one gram of 2,6-DHPN in the method (I) of oxidizing at a temperature in the range of room temperature to 80° C., and preferably 7 to 25 ml to one gram of 2,6-DHPN in the method (II) of oxidizing at a temperature in the range of 60° C. to the boiling point of the solution of the 2,6-DHPN in acetonitrile or 1,4-dioxane, and into the mixture of 2,6-DHPN and the solvent, hydrogen peroxide and the inorganic acid are added dropwise to initiate the reaction.

As the inorganic acid used in the present invention, sulfuric acid or perchloric acid is preferred, and as sulfuric acid, it is preferred to use concentrated sulfuric acid, however, diluted sulfuric acid of not less than 10% may be used.

In addition, in the case of using concentrated sulfuric acid, it may be added to the reaction system after being diluted with an aqueous solution of hydrogen peroxide or the solvent, and in the case of using perchloric acid, it is preferable to use the commerciallized aqueous solution thereof such as 70%, 60% or 40%.

In the method (I) of oxidizing at a temperature in the range of room temperature to 80° C., it is preferable to use the inorganic acid in an amount of 0.1 to 4 times by weight of the amount of 2,6-DHPN, more preferably 0.2 to 3 times by weight. In the case of using the acid in an amount of over 4 times by weight of the amount of 2,6-DHPN the selectivity in reaction is low and the low selectivity becomes the cause of coloration of the reaction product.

As the solid acid used in the present invention, acid-type ion-exchange resins, preferably those having sulfonic acid groups (-SO$_3$H), may be used.

In the method (I), it is preferable to use the solid acid in an amount of 0.1 to 5 g, more preferably 0.2 to 3 g per one g of 2,6-DHPN.

In the method (II) of oxidizing at a temperature in the range of 60° C. to the boiling point of the solution of the 2,6-DHPN in acetonitrile or 1,4-dioxane, it is preferable to use the inorganic acid in an amount of not less than 0.001 time and less than 0.1 time by weight of the amount of 2,6-DHPN, more preferably from 0.005 to 0.05 time by weight. In the case where the amount of the added inorganic acid is less than 0.001 time by weight, the reaction is not completed.

As hydrogen peroxide used in the method (I) of the present invention, the concentration of the aqueous hydrogen peroxide solution is not lower than 25% and the commerciallized aqueous 30% solution is preferable and hydrogen peroxide may be used in an amount of from 2 to 10 moles, preferably from 2 to 3 moles to one mol of 2,6-DHPN. In the case of using below 2 moles of hydrogen peroxide to one mole of 2,6-DHPN, the conversion of 2,6-DHPN into 2,6-dihydroxynaphthalene is low, and on the other hand, in the case of using over 10 moles to one mole of 2,6-DHPN, the coloration of the reaction product is remarkable.

In the method (II), the concentration of the aqueous hydrogen peroxide solution is not lower than 60%.

In adding both the inorganic acid and hydrogen peroxide to the mixture of 2,6-DHPN and the solvent by a method of dropping, etc., it is preferable to add a mixture thereof or add the inorganic acid after the addition of hydrogen peroxide.

In the case of adding the inorganic acid in preference to hydrogen peroxide, olefin is formed by the dehydration of 2-hydroxy-2-propyl group of 2,6-DHPN, and the olefin further reacts to form impurities, and accordingly, such a mode of addition is not preferable.

After the reaction is over, for instance, an aqueous saturated solution of sodium chloride is added to separate the organic layer, and after washing the organic layer with the aqueous saturated solution of sodium chloride, the solvent is distilled off from the organic layer to obtain 2,6-dihydroxynaphthalene in a yield of higher than 75%, preferably higher than 90%.

By recrystallizing the thus obtained crude 2,6-dihydroxynaphthalene from a suitable solvent, for instance, acetic acid, it is possible to obtain the purified 2,6-dihydroxynaphthalene.

2,6-Diacetoxynaphthalene is obtained by subjecting the thus obtained 2,6-dihydroxynaphthalene to acetylation.

Although there are various processes of acetylation, the process of heating 2,6-dihydroxynaphthalene together with acetic anhydride is most preferable for obtaining highly pure 2,6-diacetoxynaphthalene.

Acetic anhydride may be used in excess and also a mixture of a small excess of acetic anhydride and acetic acid may be used in acetylation.

The reaction temperature of acetylation is preferably 100° to 140° C., and the reaction is carried out for 30 min to 2 hours, the reaction completing within the above-mentioned period.

After the reaction is over, the reaction mixture is allowed to cool, is filtered to collect the crystals of 2,6-diacetoxynaphthalene.

Although the purity of the thus collected 2,6-diacetoxynaphthalene is higher than 98%, it is possible to obtain 2,6-diacetoxynaphthalene of a purity of higher than 99.5% by recrystallizing the thus obtained crystals from a suitable solvent, for instance, acetic acid.

As has been described above, according to the present invention, while using, as the starting substance, 2,6-DHPN which is easily available from 2,6-diisopropylnaphthalene which is industrially easily available, it has been possible to obtain 2,6-dihydroxynaphthalene and 2,6-diacetoxynaphthalene of a purity of higher than 95%, which are useful as the starting substances for producing aromatic polyesters having an ability of forming liquid crystals, in high yields as will be seen in the following Examples. Consequently, the process of the present invention is useful in the production of the liquid crystal polymer of aromatic polyesters.

The present invention is illustrated more in detail in the following Examples; however, it should be recognized that the scope of the present invention is not restricted to these Examples.

EXAMPLE 1

In 25 ml of acetonitrile, 1.0 g (4.1 mmole) of 2,6-DHPN was suspended, and 1.3 ml of an aqueous 31% solution of hydrogen peroxide and 0.9 ml of an aqueous 70% solution of perchloric acid were successively added, and the thus formed mixture was stirred for 10 min in an oil bath kept at 30° C.

After the reaction was over, an aqueous saturated solution of sodium chloride was added to the reaction mixture to separate the layer of acetonitrile, and the layer of acetonitrile was washed repeatedly with the saturated solution of NaCl until the layer of acetonitrile became neutral. After drying the layer of acetonitrile over anhydrous sodium sulfate, acetonitrile was distilled off, and the residue was dried to obtain 0.63 g of crude 2,6-dihydroxynaphthalene in a yield of 96.0%.

EXAMPLE 2

In 127 ml of acetonitrile, 5.0 g (20.5 mmole) 2,6-DHPN were suspended, and 6.7 ml of an aqueous 31% solution of hydrogen peroxide and 10.2 ml of a 40% solution of sulfuric acid in acetonitrile were successively added to the suspension.

The thus formed mixture was stirred for 30 min in an oil bath kept at 30° C.

After the reaction was over, the reaction mixture was treated in the same manner as in Example 1 to obtain 3.17 g of crude 2,6-dihydroxynaphthalene in a yield of 96.7%.

EXAMPLE 3

In 2 g of acetonitrile, 0.1 g (0.41 mmole) of 2,6-DHPN was suspended, and 0.15 g of an aqueous 31% solution of hydrogen peroxide and 0.3 g of an aqueous 40% solution of perchloric acid were successively added to the suspension.

The thus formed mixture was stirred for 30 min at 30° C.

As a result of examining the reaction mixture by high performance liquid chromatography (HPLC), it was found that 2,6-dihydroxynaphthalene was nearly quantitatively formed therein.

EXAMPLE 4

Into a mixture of 0.2 g (0.82 mmole)of 2,6-DHPN, 2 g of 1,4-dioxane and 0.35 g of an aqueous 31% solution of hydrogen peroxide, 0.5 g of an aqueous 40% solution of perchloric aid was added dropwise under stirring at 40° C. and the thus formed mixture was further stirred for 30 min at 40° C.

As a result of examining the reaction mixture by HPLC, it was found that 2,6-dihydroxynaphthalene was formed in a yield of 98%.

EXAMPLE 5

After adding dropwise a mixture of 0.3 g of concentrated sulfuric acid and 0.3 g of an aqueous 31% solution of hydrogen peroxide to a mixture of 0.2 g (0.82 mmole) of 2,6-DHPN and 1.5 g of 1,4-dioxane, the thus formed mixture was stirred for 30 min at 30° C.

As a result of examining the reaction mixture by HPLC, it was found that 2,6-dihydroxynaphthalene was formed in a yield of 99%.

EXAMPLE 6

In 23 ml of acetonitrile, 1 g (4.1 mmole) of 2,6-DHPN was suspended, and 1.3 ml of an aqueous 31% solution of hydrogen peroxide and 2 g (dry) of AMBERLITE 200C (H-type) (made by ORGANO Inc., Tokyo, Japan) were successively added into the thus obtained suspension.

The thus formed mixture was stirred for 2 hours at 50° C.

As a result of examining the reaction mixture by HPLC, 2,6-dihydroxynaphthalene was formed in a yield of 93%.

EXAMPLE 7

In 920 ml of acetonitrile, 50.0 g (0.205 mole) of 2,6-DHPN were suspended, and 55 g of an aqueous 31% solution of hydrogen peroxide and 50 g of a 40% solution of sulfuric acid in acetonitrile were successively added to the thus formed suspension. The thus formed mixture was stirred for 40 min in an oil bath kept at 30° C.

After the reaction was over, an aqueous saturated solution of sodium chloride was added to the reaction mixture to separate the organic layer, and the organic layer was washed repeatedly with the aqueous saturated solution of sodium chloride until the organic layer became neutral. After drying the organic layer over anhydrous sodium sulfate, acetonitrile was distilled off therefrom, and the residue was dried to obtain 34.8 g of 2,6-dihydroxynaphthalene in a yield of 96.0%.

Thereafter, a mixture of 33.2 g (0.187 mole) of the thus obtained 2,6-dihydroxynaphthalene, 15.0 g of acetic acid and 44.9 g of acetic anhydride was stirred for 90 min in an oil bath kept at 140° C. After the reaction was over, the reaction mixture was cooled to room temperature and the thus precipitated crystals were collected by filtration, washed with acetic acid and dried to obtain 41.8 g of 2,6-diacetoxynaphthalene of white in color in a yield of 91.7%.

As a result of examining the purity of the thus obtained 2,6-diacetoxynaphthalene by a differential scanning calorimeter (DSC, Mettler TA 3000 System), the purity was 99.81%.

In addition, 1.75 g of 2,6-diacetoxynaphthalene of the purity of 91.3% (by a high performance liquid chromatography) were further obtained from the mother liquor. Namely, the combined yield of 2,6-diacetoxynaphthalene became 95.2%.

Subsequently, 41.0 g of 2,6-diacetoxynaphthalene of the purity of 99.81% were recrystallized from 61.5 g of acetic acid to obtain 39.3 g of 2,6-diacetoxynaphthalene of a high purity of 100% (by HPLC) and 99.97% (by DSC) in a recovery of 95.8%. In addition, from the mother liquor of recrystallization, 1.3 g of 2,6-diacetoxynaphthalene were further obtained, and therefore the combined recovery became 99.0%.

EXAMPLE 8

In 400 ml of acetonitrile, 70.0 g (0.287 mole) of 2,6-DHPN were suspended, and 70.0 g of an aqueous 31% solution of hydrogen peroxide and 52.5 g of a 40% solution of sulfuric acid in acetonitrile were successively added to the thus formed suspension, and the mixture was stirred for 30 min in an oil bath kept 30° C.

After the reaction was over, an aqueous saturated solution of sodium chloride was added to the reaction mixture to separate the acetonitrile layer. After neutralizing the acetonitrile layer with sodium carbonate and then drying the thus neutralized acetonitrile layer over anhydrous sodium sulfate, acetonitrile was distilled off from the layer to obtain 45.14 g 2,6-dihydroxynaphthalene in a yield of 98.5%.

Subsequently, 45 g of the thus obtained 2,6-dihydroxynaphthalene were acetylated with 23 g of acetic acid and 61 g of acetic anhydride in the same manner as in Example 7 to obtain 60.6 g of 2,6-diacetoxynaphthalene of the purity of 99.85% (by DSC) in a yield of 93.0%.

EXAMPLE 9

In 250 ml of acetonitrile, 10.0 g (0.041 mole) of 2,6-DHPN were dispersed, and 15 g of an aqueous 31% solution of hydrogen peroxide and 30 g of an aqueous 40% solution of perchloric acid were added to the thus formed dispersion, and the thus formed mixture was stirred for 30 min at 30° C. After the reaction was over, the reaction mixture was treated as in Example 7 to obtain 6.7 g of 2,6-dihydroxynaphthalene in a yield of 96.5%.

Subsequently, 6.0 g (0.035 mol) of the thus obtained 2,6-dihydroxynaphthalene were acetylated with 2.7 g of acetic acid and 7.9 g of acetic anhydride in the same manner as in Example 7 to obtain 7.9 g of 2,6-diacetoxynaphthalene of white in color in a yield of 92.5%.

The purity of the thus obtained 2,6-diacetoxynaphthalene was 99.85% (by DSC).

EXAMPLE 10

A mixture of 20.0 g (0.082 mole) of 2,6-DHPN, 200 ml of 1,4-dioxane and 35 g of an aqueous 31% solution of hydrogen peroxide was stirred at 40° C., and 50 g of an aqueous 40% solution of perchloric acid were added dropwise, and the thus formed mixture was stirred for further 30 min after completion of the addition. After the reaction was over, the reaction mixture was treated as in Example 7 to obtain 13.5 g of 2,6-dihydroxynaphthalene in a yield of 97.8%.

In the same manner as in Example 7, 13.0 g of the thus obtained 2,6-dihydroxynaphthalene were acetylated with 5.9 g of acetic acid and 17.6 g of acetic anhydride to obtain 17.5 g of 2,6-diacetoxynaphthalene of the purity of 99.82% (by DSC).

EXAMPLE 11

In 250 ml of acetonitrile, 10.0 g (0.041 mole) of 2,6-DHPN were suspended, and 13 ml of an aqueous 31% solution of hydrogen peroxide and 9 ml of an aqueous 70% solution of perchloric acid were successively added to the thus formed suspension. The thus formed mixture was stirred for 30 min in an oil bath kept at 30° C. After the reaction was over, the reaction mixture was treated as in Example 7 to obtain 6.6 g of 2,6-dihydroxynaphthalene in a yield of 95.6%.

In the same manner as in Example 7, 6.0 g of the thus obtained 2,6-dihydroxynaphthalene were acetylated with 2.7 g of acetic acid and 7.9 g of acetic anhydride to obtain 8.0 g of 2,6-diacetoxynaphthalene of the purity of 99.85% (by DSC).

EXAMPLE 12

In 23 ml of acetonitrile, 1 g (4.1 mmole) of 2,6-DHPN was suspended, and 1.3 ml of an aqueous 31% solution of hydrogen peroxide and 2 g (dry) of AMBERLITE 200C (H-type) (made by ORGANO Inc., Tokyo, Japan) were successively added into the thus obtained suspension.

The thus formed mixture was stirred for 2 hours at 50° C.

As a result of examining the reaction mixture by HPLC, 2,6-dihydroxynaphthalene was formed in a yield of 93%.

In the same manner as in Example 7, 0.6 g of the thus obtained 2,6-dihydroxynaphthalene were acetylated with 0.27 g of acetic acid and 0.79 g of acetic anhydride to obtain 0.83 g of 2,6-diacetoxynaphthalene of the purity of 99.80% (by DSC).

COMPARATIVE EXAMPLES 1 to 3

In the same manner as in Examples 1 to 3, each of the three reactions was carried out except for using acetic acid instead of using acetonitrile in Examples 1 to 3. On analyzing the thus obtained reaction mixture by gas-chromatography, any formation of 2,6-dihydroxynaphthalene was not recognized, although 2,6-DHPN disappeared from the reaction mixture.

COMPARATIVE EXAMPLE 4

Into a mixture of 0.1 g (0.41 mmol) of 2,6-DHPN, 2 g of ethanol and 0.2 g of an aqueous 31% solution of hydrogen peroxide, 0.1 g of an aqueous 70% solution of perchloric acid was added and stirring was started to initiate the reaction. After 30 min from the initiation of the reaction, any formation of 2,6-dihydroxynaphthalene was not recognized. After subjecting the mixture to reaction further for 2 hours, it was found that 2,6-dihydroxynaphthalene was formed in a yield of 55%. On examining the reaction mixture by gas-chromatography, formation of a number of by-products was recognized.

COMPARATIVE EXAMPLE 5

Into a mixture of 0.1 g of 2,6-DHPN, 2.0 g of n-heptane and 0.2 g of an aqueous 31% solution of hydrogen peroxide, 0.1 g of an aqueous 70% solution of perchloric acid was added, and the thus formed mixture was stirred for 30 min at 30° C.

It was found that 2,6-dihydroxynaphthalene was formed in a yield of 53.1%, however, on examining the reaction product by gas-chromatography, formation of a number of by-products was recognized.

COMPARATIVE EXAMPLE 6

Into a mixture of 0.1 g of 2,6-DHPN, 2.0 g of benzene and 0.2 g of an aqueous 31% solution of hydrogen peroxide, 0.1 g of an aqueous 70% solution of perchloric acid was added, and the thus formed mixture was stirred at 30° C. to initiate the reaction. After 30 min from the initiation of the reaction, the formation of 2,6-dihydroxynaphthalene was very small and, the reaction was continued for further 5 hours accordingly. The yield of 2,6-dihydroxynaphthalene was 45.7%, however, precipitation of an insoluble matter black in color and unknown in structure was recognized in the reaction mixture.

COMPARATIVE EXAMPLE 7

In the same manner as in Example 7, 2,6-dihydroxynaphthalene was produced and it was recrystallized from acetic acid as follows.

In spite of repeating the recrystallization three times while using acetic acid in an amount of 3 times by weight of the amount of 2,6-dihydroxynaphthalene, the purity of the thus obtained, recrystallized 2,6-dihydroxynaphthalene was 98.8% (by DSC) and the recovery was about 50%.

In addition, it was attempted to obtain a second crop from the mother liquor, however, the mother liquor changed into a tarry matter when condensed, and as a result, the recovery of 2,6-dihydroxynaphthalene from the mother liquor was impossible.

On the contrary, as seen from Examples 5 to 9, by acetylating 2,6-dihydroxynaphthalene, 2,6-diacetoxynaphthalene of a high purity is obtained in high yields.

REFERENCE EXAMPLE

Into 20 ml of acetone, 1.0 g of an aqueous 31% solution of hydrogen peroxide and 2.0 g of an aqueous 70% solution of perchloric acid were added, and the mixture was stirred for 30 min at 30° C. to obtain a white precipitate. The thus obtained precipitate had a stimulative odor and was considered to be a condensate of acetone. It was found that acetone was not inert in the reaction system according to the present invention and that acetone is not suitable as the reaction solvent therein.

EXAMPLE 13

Into 240 ml of acetonitrile, 10.0 g (41 mmole) of 2,6-DHPN were dissolved at 70° C., and 4 ml of an aqueous 70% solution of hydrogen peroxide were added to the thus formed solution. Then, a solution of 0.1 g of concentrated sulfuric acid in 10 ml of acetonitrile was added to the thus formed mixture, and the whole mixture was reacted under agitation for 20 min in an oil bath kept at 70° C. After the reaction was over, an aqueous saturated saline solution was added to the liquid reaction mixture and after separating the acetonitrile layer, the thus obtained acetonitrile layer was washed with an aqueous saturated saline solution until the acetonitrile layer became neutral. After separating the acetonitrile layer, the solvent was distilled off from the acetonitrile layer and the residue was dried to obtain 6.6 g of crude 2,6-dihydroxynaphthalene (yield : 99%).

EXAMPLE 14

The reaction was carried out in the same manner as in Example 13 except for using 1,4-dioxane instead of acetonitrile in Example 13. On quantitatively analyzing the thus obtained reaction mixture with the high performance liquid chromatography, 2,6-dihydroxynaphthalene was obtained (yield: 99%).

What is claimed is:

1. A process for producing 2,6-dihydroxynapththa- lene, which comprises oxidizing 2,6-di(2-hydroxy-2-propyl)naphthalene in acetonitrile, 1,4-dioxane or a mixture thereof with hydrogen peroxide in the presence of an inorganic acid or a solid acid at a temperature in the range of room temperature to the boiling point of the solution of 2,6-di(2-hydroxy-2-propyl)naphthalene in acetonitrile or 1,4-dioxane, said acetonitrile, 1,4-dioxane or a mixture thereof being used in an amount of 3 to 30 ml to one gram of said 2,6-di(2-hydroxy-2-propyl)-naphthalene.

2. A process according to claim 1, wherein said inorganic acid is sulfuric acid or perchloric acid.

3. A process according to claim 1, wherein said solid acid is an ion-exchange resin having sulfonic acid groups.

4. A process according to claim 1, wherein the oxidation of 2,6-di(2-hydroxy-2-propyl)naphthalene is carried out in acetonitrile, 1,4-dioxane or a mixture thereof of an amount of 5 to 20 ml to one gram of said 2,6-di(2-hydroxy-2-propyl)naphthalene and at a temperature in the range of room temperature to 80° C.

5. A process according to claim 4, wherein the oxidation of said 2,6-di(2-hydroxy-2-propyl)naphthalene is carried out in the presence of the inorganic acid of an amount of 0.1 to 4 times by weight of the amount of 2,6-di(2-hydroxy-2-propyl)naphthalene.

6. A process according to claim 5, wherein the oxidation of said 2,6-di(2-hydroxy-2-propyl)naphthalene is carried out in the presence of the inorganic acid of an amount of 0.2 to 3 times by weight of the amount to the 2,6-di(2-hydroxy-2-propyl)naphthalene.

7. A process according to claim 4, wherein the oxidation of said 2,6-di(2-hydroxy-2-propyl)naphthalene is carried out by using hydrogen peroxide of an amount of from 2 to 10 moles to one mole of said 2,6-di(2-hydroxy-2-propyl)naphthalene.

8. A process according to claim 7, wherein the concentration of the aqueous hydrogen peroxide solution is not lower than 25%.

9. A process according to claim 4, wherein the oxidation of 2,6-di(2-hydroxy-2-propyl)naphthalene is carried out in the presence of solid acid of an amount of 0.1 to 5 times by weight of the amount of said 2,6-di(2-hydroxy-2-propyl)naphthalene.

10. A process according to claim 1, wherein the oxidation of 2,6-di(2-hydroxy-2-propyl)naphthalene carried out in acetonitrile, 1,4-dioxane or a mixture thereof of an amount of 7 to 25 ml to one gram of said 2,6-di(2-hydroxy-2-propyl)naphthalene and at a temperature in the range of 60° C. to the boiling point of the solution of said 2,6-di(2-hydroxy-2-propyl)naphthalene in acetonitrile or 1,4-dioxane.

11. A process according to claim 10, wherein the oxidation of said 2,6-di(2-hydroxy-2-propyl)naphthalene is carried out in the presence of the inorganic acid of an amount not less than 0.001 time by weight and less than 0.1 time by weight to the amount of the 2,6-di(2-hydroxy-2-propyl)naphthalene.

12. A process according to claim 11, wherein oxidation of said 2,6-di(2-hydroxy-2-propyl)naphthalene is carried out in the presence of the inorganic acid of an amount of from 0.005 to 0.05 time by weight of the amount to the 2,6-di(2-hydroxy-2-propyl)naphthalene.

13. A process according to claim 10, wherein the oxidation of said 2,6-di(2-hydroxy-2-propyl)naphthalene is carried out by using hydrogen peroxide of an amount of from 2 to 3 moles to one mole of said 2,6-di(2-hydroxy-2-propyl)naphthalene.

14. A process according to claim 13, wherein the concentration of the aqueous hydrogen peroxide solution is not lower than 60%.

15. A process according to claim 1, wherein said 2,6-dihydroxynaphthalene is further acetylated at a temperature of 100° to 140° C. for 30 minutes to 2 hours thereby obtaining 2,6-diacetoxynaphthalene.

16. A process according to claim 15, wherein the acetylation of 2,6-dihydroxynaphthalene is carried out in acetic anhydride or a mixture of acetic anhydride and acetic acid.

17. A process for producing 2,6-diacetoxynaphthalene, which comprises acetylating 2,6-dihydroxynaphthalene, produced by the process which comprises oxidizing 2,6-di(2-hydroxy-2-propyl)naphthalene in acetonitrile, 1,4-dioxane or a mixture thereof with hydrogen peroxide in the presence of an inorganic acid or a solid acid at a temperature in the range of room temperature to the boiling point of the solution of 2,2,6-di(2-hydroxy-2-propyl)naphthalene in acetonitrile or 1,4-dioxane, said acetonitrile, 1,4-dioxane or a mixture thereof being used in an amount of 3 to 30 ml to one gram of said 2,6-di(2-hydroxy-2-propyl)naphthalene, at a temperature of 100° to 140° C. for 30 minutes to 2 hours in acetic anhydride or a mixture of acetic anhydride and acetic acid.

* * * * *